United States Patent
Lechner et al.

(10) Patent No.: US 9,746,455 B2
(45) Date of Patent: Aug. 29, 2017

(54) PORTABLE ELECTRONIC DEVICE WITH INTEGRATED CHEMICAL SENSOR AND METHOD OF OPERATING THEREOF

(71) Applicant: Sensirion AG, Stafa (CH)

(72) Inventors: Moritz Lechner, Uerikon (CH); Johannes Buhler, Uster (CH); Rafael Santschi, Zurich (CH)

(73) Assignee: Sensirion AG, Stafa (CH)

( * ) Notice: Subject to any disclaimer, the term of this patent is extended or adjusted under 35 U.S.C. 154(b) by 491 days.

(21) Appl. No.: 14/161,225

(22) Filed: Jan. 22, 2014

(65) Prior Publication Data

US 2014/0208829 A1    Jul. 31, 2014

(30) Foreign Application Priority Data

Jan. 31, 2013 (EP) .................................. 13405027

(51) Int. Cl.
*G01N 33/00* (2006.01)
*G01N 33/497* (2006.01)
(Continued)

(52) U.S. Cl.
CPC ...... *G01N 33/497* (2013.01); *H04M 1/72525* (2013.01); *G01N 27/122* (2013.01);
(Continued)

(58) Field of Classification Search
CPC ........... G01N 33/0004; G01N 33/0009; G01N 33/0031; G01N 33/0037; G01N 33/0047
See application file for complete search history.

(56) References Cited

U.S. PATENT DOCUMENTS

| | | | |
|---|---|---|---|
| 4,428,685 A | * | 1/1984 | Lemelson ................ G01B 3/18 374/163 |
| 5,234,835 A | * | 8/1993 | Nestor ................ A61B 5/1459 422/82.06 |

(Continued)

FOREIGN PATENT DOCUMENTS

CN    202734862 U  *  2/2013

OTHER PUBLICATIONS

Heng I., et al., "A Unique Environmental Mobile Device for Detecting Hazardous Chemicals", Global Humanitarian Technology Conference (GHTC), 2012 IEEE, Oct. 21, 2012 (Oct. 21, 2012), pp. 59-65.*

(Continued)

*Primary Examiner* — David A Rogers
(74) *Attorney, Agent, or Firm* — Cooper & Dunham LLP

(57) ABSTRACT

A portable electronic device and related methods are described using an integrated chemical sensor linked to a chemical sensor processing unit and being sensitive to the concentration of a component in a sample of air and further including an operating system providing instructions for the control of the portable device, wherein the chemical processing unit uses under operating conditions a first set of instructions and a second set of instructions stored within the portable device, wherein the first set of instructions is part of the operating system level of instructions and the second set of instructions is part of a user of instructions with the second set of instructions being linked to the operating system via a plugin interface and wherein the second set of instructions is communicated to the portable device from a remote computing system based on access to measurements and/or operating conditions of the chemical sensor.

18 Claims, 3 Drawing Sheets

(51) Int. Cl.
*H04M 1/725* (2006.01)
*G01N 27/12* (2006.01)
*G06F 9/445* (2006.01)

(52) U.S. Cl.
CPC .............. *G01N 27/128* (2013.01); *G06F 8/65* (2013.01); *H04M 2250/12* (2013.01)

(56) References Cited

U.S. PATENT DOCUMENTS

| | | | | |
|---|---|---|---|---|
| 5,716,506 A * | 2/1998 | Maclay | ............ | G01N 27/4045 204/424 |
| 5,993,743 A * | 11/1999 | Nordman | ............ | G01N 1/2252 250/339.13 |
| 6,244,093 B1 * | 6/2001 | Parekh | ............ | G01N 33/0006 73/1.06 |
| 6,289,288 B1 * | 9/2001 | Kraft | ............ | G01N 33/0006 204/401 |
| 6,605,038 B1 * | 8/2003 | Teller | ............ | A61B 5/411 128/904 |
| 6,744,373 B2 * | 6/2004 | Koyano | ............ | G08B 21/14 324/464 |
| 6,782,351 B2 * | 8/2004 | Reichel | ............ | G01N 33/0075 340/501 |
| 6,790,178 B1 * | 9/2004 | Mault | ............ | A61B 5/0011 128/903 |
| 7,279,688 B2 * | 10/2007 | Campman | ............ | G01N 21/645 250/301 |
| 7,319,385 B2 * | 1/2008 | Ruha | ............ | A61B 5/02055 340/539.12 |
| 8,077,042 B2 * | 12/2011 | Peeters | ............ | A61B 5/0002 340/539.12 |
| 8,616,452 B2 * | 12/2013 | Isuyama | ............ | G11B 5/00808 235/449 |
| 8,795,596 B2 * | 8/2014 | Helwig | ............ | G01N 27/125 422/82.01 |
| 8,957,631 B2 * | 2/2015 | Ramsesh | ............ | G01D 5/2013 320/108 |
| 9,189,944 B2 * | 11/2015 | Johnson, Jr. | ............ | G06K 7/0095 |
| 9,328,698 B2 * | 5/2016 | MacNeille | ............ | F02D 37/02 |
| 9,341,131 B2 * | 5/2016 | Weber | ............ | F02D 41/064 |
| 2001/0003249 A1 * | 6/2001 | Stormbom | ............ | G01N 27/223 73/1.06 |
| 2001/0018844 A1 * | 9/2001 | Parekh | ............ | G01N 33/0006 73/1.06 |
| 2001/0050612 A1 * | 12/2001 | Shaffer | ............ | G08B 7/06 340/521 |
| 2003/0145644 A1 * | 8/2003 | Rabbett | ............ | G01N 33/0006 73/1.06 |
| 2003/0167345 A1 * | 9/2003 | Knight | ............ | B60R 16/0315 709/249 |
| 2004/0081582 A1 * | 4/2004 | Brooke | ............ | G01N 33/497 422/62 |
| 2004/0163445 A1 * | 8/2004 | Dimeo, Jr. | ............ | G01N 27/128 73/23.2 |
| 2005/0053523 A1 * | 3/2005 | Brooke | ............ | G01N 33/4972 422/68.1 |
| 2005/0272447 A1 * | 12/2005 | Eckel | ............ | G01C 5/06 455/456.6 |
| 2006/0042353 A1 * | 3/2006 | Marquis | ............ | G01N 33/0031 73/23.2 |
| 2006/0193749 A1 * | 8/2006 | Ghazarian | ............ | A61B 5/083 422/83 |
| 2006/0220888 A1 * | 10/2006 | Germouni | ............ | G01J 5/522 340/605 |
| 2006/0263254 A1 * | 11/2006 | Lee | ............ | G01N 33/0006 422/83 |
| 2007/0005267 A1 * | 1/2007 | Li | ............ | H04M 1/72522 702/24 |
| 2007/0241261 A1 * | 10/2007 | Wendt | ............ | G01D 9/005 250/221 |
| 2007/0296569 A1 * | 12/2007 | Bray | ............ | G08B 21/14 340/506 |
| 2008/0161711 A1 * | 7/2008 | Orr | ............ | A61B 5/0833 600/532 |
| 2009/0090626 A1 * | 4/2009 | Holt et al. | ............ | G01N 33/005 204/431 |
| 2009/0218235 A1 * | 9/2009 | McDonald | ............ | G01N 27/127 205/775 |
| 2009/0227287 A1 * | 9/2009 | Kotidis | ............ | G01J 3/02 455/556.1 |
| 2010/0222648 A1 * | 9/2010 | Tan | ............ | A61B 5/0022 600/301 |
| 2010/0234064 A1 * | 9/2010 | Harris, Jr. | ............ | B60K 28/066 455/556.1 |
| 2010/0273665 A1 * | 10/2010 | Haick | ............ | B82Y 15/00 506/8 |
| 2011/0178420 A1 * | 7/2011 | Ridder | ............ | A61B 5/14546 600/532 |
| 2012/0032692 A1 * | 2/2012 | Kothari | ............ | G01N 27/227 324/672 |
| 2012/0206497 A1 * | 8/2012 | Sarjanoja | ............ | G06F 3/0481 345/672 |
| 2012/0221254 A1 * | 8/2012 | Kateraas | ............ | A61B 5/02055 702/19 |
| 2013/0174646 A1 * | 7/2013 | Martin | ............ | G01N 33/00 73/31.02 |
| 2013/0241738 A1 * | 9/2013 | Kastli | ............ | G08B 17/10 340/686.4 |
| 2013/0341206 A1 * | 12/2013 | Schenk | ............ | G01N 27/30 205/780.5 |
| 2014/0238100 A1 * | 8/2014 | Londergan | ............ | G01N 33/0006 73/1.03 |
| 2016/0220194 A1 * | 8/2016 | Kang | ............ | A61B 5/7278 |

OTHER PUBLICATIONS

Bai, Gang, "Mobile Phone Programming—Based on Mobile Sensor API for User Interface", Retrieved at <<https://publications.theseus.fi/bitstream/handle/10024/14108/Bai_Gang.pdf>>, May 10, 2010, pp. 75.*
P. Wu, et al., "MobiSens: A Versatile Mobile Sensing Platform for Real-World Applications", Mobile Newtw Appl. (2013); 18:60-80.
A. Mane, et al., "Explosive Detection With Mobile Telephony, An Attempt Towards a Safe Ambience", International Conference on Signal Processing, Communication, Computing and Networking Technologies, 2011, pp. 187-191.
M. Karst, et al., "Humidity and Temperature Sensors in Mobile Phones", Sensirion AG, Switzerland, Apr. 18, 2012.

* cited by examiner

PORTABLE ELECTRONIC DEVICE WITH INTEGRATED CHEMICAL SENSOR AND METHOD OF OPERATING THEREOF

FIELD OF THE INVENTION

The present invention relates to a portable electronic device such as a mobile phone, tablet and the like with an integrated chemical sensor with the sensor being located within the exterior shell or housing of the device and methods of operating the sensor.

BACKGROUND OF THE INVENTION

Portable or mobile devices originally introduced as mobile phones or electronic agendas become more and more ubiquitous. As the processing power of their internal processors grows and equally the bandwidth for communication with stationary processors, such portable devices take on more and more the role of multi-purpose tools available to consumers and specialist users alike.

It has been recognized that portable devices can benefit from the presence of sensors capable of providing chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

It has been known to incorporate gas sensors into portable sensor devices, such as mobile phones or tablet computers. For example, humidity sensors have been incorporated into some smartphone devices. However, humidity (i.e. gaseous water in air) is only one gas that might be of interest to a user of this type of device. Therefore, there is a need to provide devices that allow to measure a larger selection of gases, such as alcohol, CO, benzene, or groups of gases, which can e.g. be classified as certain smells or odors.

Even though there are various sensor types, in particular metal-oxide gas sensors, that allow detection of such gases or groups of gases these sensors are typically not very selective and are more or less sensitive to whole classes of gases. In order to distinguish between certain gases or groups of gases, a plurality of sensors may have to be combined and/or a sensor must be operated in a certain fashion, e.g. using a certain temperature profile. In addition, the results of a measurement are typically processed using predefined routines and methods, which are specific to the sensor and the type of gas or gases to be measured.

General purpose portable device are known to be operated using an operation system (OS). To expand the versatility of such devices, it is further known to provide a mechanism for running third party software applications on these devices. For this purpose, the devices are provided with an application programming interface (API), which provides calls or handlers for the exchange of data with the device's OS in a standardized manner. An example of an API for a gas sensor is the Environment Sensors API of the Android operating system. In particular, this API supports humidity sensors, which measure the humidity of the ambient air.

However both the performance of an individual sensor integrated into the portable device as well as the routines to operate it and to evaluate the measurement can be subject to change. These changes can be for example a deterioration of the sensor performance or improvements in the methods used to evaluate the results.

In view of the above problems it is seen as an object of the invention to provide a portable electronic device with an adaptable chemical sensor system located within its housing and related methods for providing an adaptable control of the chemical sensor.

SUMMARY OF THE INVENTION

Hence, according to a first aspect of the invention, there is provided a method of operating a portable electronic device, preferably with telecommunication capabilities to allow for data and/or voice communication via private or public networks, enclosed in a housing having preferably an air duct with an opening to the exterior of the housing and at least one chemical sensor controlled by a chemical sensor processing unit being part of a locally stored operating system providing instructions for the control of the portable device, wherein the chemical processing unit uses under operating conditions a first set of instructions and a second set of instructions stored within the portable device, wherein the first set of instructions is part of the operating system level of instructions and the second set of instructions is part of a user level of instructions with the second set of instructions being linked to the operating system via a sensor plugin interface and wherein the second set of instructions is communicated to the portable device from a remote computing system having access to measurements and/or operating conditions of the chemical sensor.

The novel method allows for improved control of a chemical sensor integrated into a general purpose portable device. Typically sensors integrated into such a device are operated by the operating system (OS) of the device and its sensor specific extensions such as libraries etc. Any change in the control and operation of the sensor requires an update of the OS. However, it is desirable to improve the performance of the sensor outside the update cycle of the OS. It is also desirable to provide user specific updates. Both objects can be achieved by providing a set of instructions above the OS level in what is commonly known as the user or app level and accessible for the storage and running of applications from third parties other than the provider of the operating system.

In a preferred embodiment the storage location or file space used to store the second set of instructions is at least partly reserved by the operating system for storage of the second set of instructions. In this specific embodiment the file space for updates is protected and, when assigned in a predefined manner, can be made accessible through the sensor plugin interface which handles for example calls from routines being part of the first set of instructions.

In a further preferred embodiment the second set of instructions includes instructions specific to the portable device, its chemical sensor and/or its usage. These instructions can be derived remotely by monitoring the measurements, the results and any other information related to the specific use of the sensor within a specific device.

After a linking process through the plugin interface the second set of instructions are preferably handled by the operating system essentially in the same manner as the control and processing routines already stored as first set of instructions. The second set can thus include any information required to perform, improve, select and even replace such routines.

The presence of an update including a second set of instructions is preferably communicated via a downloading application as push notification. The downloading application can also be authorized and used to ensure that the update is stored at the prescribed location.

A preferred chemical sensor includes a sensor material, preferably in form of a layer, also denoted as receptor layer, to which an analyte may bond to and as such modify an electrical property of the sensor material such as its electrical conductance, e.g. metal oxide chemical sensors. It can also include a plurality of different sensors or an array of similar sensors. In such a sensor array, each sensor cell may provide a layer of material exhibiting different absorption characteristics such that each cell of the sensor array may specifically be sensitive to a different analyte and as such may enable the portable electronic device to detect the presence or absence or concentration of such analyte.

A preferred sensor is combined with a least part of its control and read-out circuit onto a single semiconductor substrate. In a preferred variant this circuit is a CMOS circuit.

The portable device can be a smart phone, a handheld computer, a laptop, an electronic reader, a tablet computer, a game controller, a pointing device, a photo or a video camera, a digital music player, an electronic wrist watch, a headset or a computer peripheral. Its housing is typically a shell of metal, glass, or plastic material and can be assembled as a unibody or from several parts. Enclosed in the housing are typically processors, drivers for parts such as screens, antennae, cameras, microphones and speakers as well as batteries to provide power to the device and its parts. A screen is typically arranged as a part of the housing or mounted behind a transparent window of the housing.

The duct acts as confinement for the air inside the housing and can take the shape of a tube or channel formed as part of the housing or as a separate part connected to an opening in the housing. It can be a single straight or curved duct.

The opening itself can be a dedicated opening thus exclusively connecting the chemical sensor to the outside. However, given that the manufacturers of portable electronic devices strive to maintain the housing as a good protection against humidity and water, it is seen as advantageous that the opening is shared with at least one further component of the portable device requiring a similar connection to the exterior, such as a loudspeaker or a microphone. The opening can further be protected by a grill or a membrane to prevent bigger particles or unwanted components of the air from entering or blocking the duct.

The above and other aspects of the present invention together with further advantageous embodiments and applications of the invention are described in further details in the following description and figures.

DETAILED DESCRIPTION

Figure 1A:
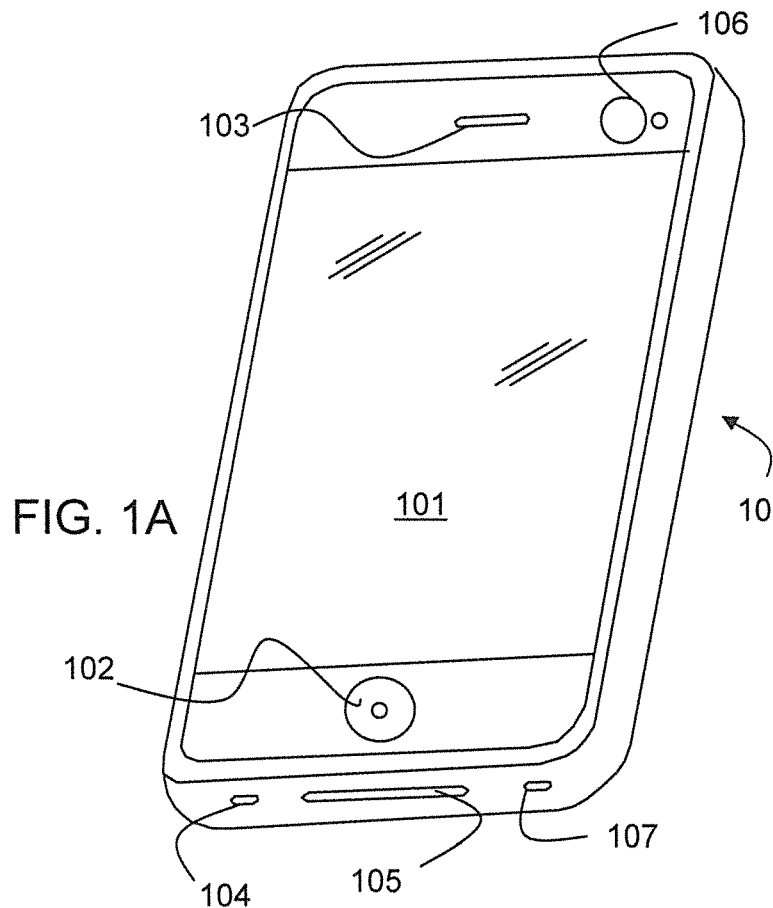
FIG. 1A is a perspective view of a portable electronic device.

The device of FIG. 1A is a portable electronic device such as a mobile phone. The housing 10 of the mobile phone includes a front side with a screen 101 and elements like buttons 102 to let a user interact with the phone. Also shown on the front side is an opening 103 for a loudspeaker. Further openings 104,105 are located at a lower side wall of the housing 10. It is well known to mount components like microphones and loudspeakers behind such openings. The phone includes one or two cameras 106, and internally additional sensors (not shown) such as location sensors or GPS, and acceleration and orientation sensors in a manner well known.

Figure 1B:
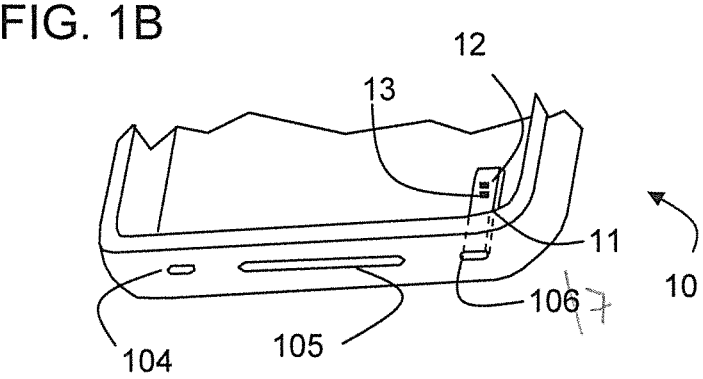
FIG. 1B is a schematic view into part of the housing of the device of FIG. 1A.

Another opening 107 is located at the lower side wall. As shown in FIG. 1B the opening 107 is linked to a tubular duct 11 passing through the interior of the housing. A chemical sensor 12 and a humidity sensor 13 are both mounted along the duct 11 such that the sensitive areas of both sensors are essentially exposed air of the same composition entering the duct through the opening 107. The actual size and shape of the duct 11 depends on the volume available and the nature of the chemical gas sensor 12 and the humidity sensor 13 can vary, but given the physical constraints of portable mobile devices the area of the opening is typically in the range of less than 10 square millimeters and in the present example actually about less than 3.1 square millimeters.

Figure 2:
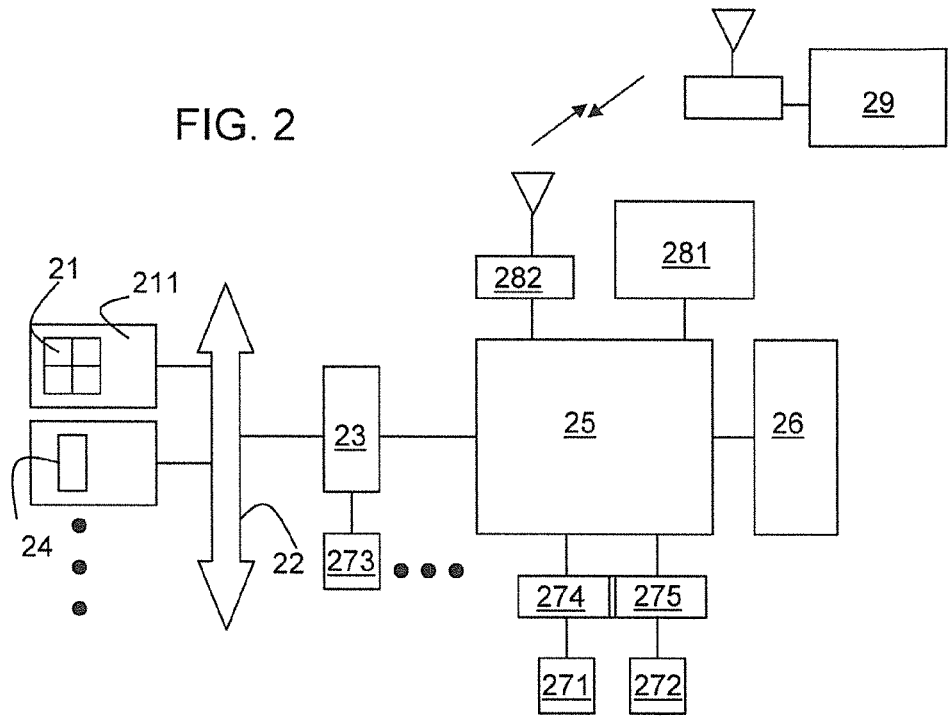
FIG. 2 is a block diagram with components of a portable device in accordance with an example of the invention.

FIG. 2 shows a block diagram with the most important components of the portable device. In particular, the device includes a chemical gas sensor 21 integrated as part of a CMOS substrate 211 which has CMOS circuitry to control the basic functions and the basic readout of the sensor. The CMOS circuit can include for example the driver to switch the sensor and his heater on or off as well as A/D converters and amplifiers and an I2C bus controller to exchange data on an I2C bus 22. The I2C bus connects the sensors with a sensor hub 23. A further humidity and temperature sensor 24 is also linked to the I2C bus 22. The chemical sensor 21 can be for example a single sensor, such as a metal oxide type sensor, or an array or assembly of several sensors. The chemical sensors can be either of the same type of metal oxide sensors but with a different sensing material or, either alternatively or in addition, sensors based on a different sensing principle.

The sensor hub 23 provides a control and processing unit for more complex control and read-out functions of the chemical sensor 21 based on signals sent to or extracted from, respectively, the on-chip CMOS circuitry.

Further control and read-out function can also be performed by the central processing unit (CPU)25 of the portable device, which in turn has read/write access to a memory 26, which can include static or volatile memory or both as known in the art. The memory 26 typically stores the operating system of the device and can also be used to store application programs specific to the operation of the sensors of the portable device.

In addition to the specific sensors as described above, the CPU is also connected to one or more sensors, for example the camera 271 or the microphone 272 also shown as the camera 106 and the microphone 104 of FIG. 1. Other examples are location, acceleration and orientation sensors 273, which are shown linked to the sensor hub 23. The sensors 271, 272 communicate with the CPU 25 using their own interface units 274, 275, respectively, which operate typically in complete independence of the chemical sensor 21.

The device includes further well known input/output units 281 such as a touch sensitive display, virtual or physical keyboards and gesture tracking devices etc. The portable device as shown has a telecommunication circuit 282 comprising an antenna, driver circuits and encoding and decoding units as are well known in the art. Using such a telecommunication circuit, the device can connect to remote data processing and storage facilities 29 as shown.

The FIGS. 3A and 3B shows components of the software stack as used to operate a portable device with integrated chemical sensor as described above. The software stack as residing in dedicated or general memory within the portable device comprises a kernel 30 adapted to provide low-level functionality. The kernel e.g. comprises the individual device drivers adapted to interact with individual hardware components of the device.

The sensor hub 23 of FIG. 2 is implemented as a programmable microcontroller that runs its own kernel software 31, which interacts with a hub driver 32 of the main kernel 30. The driver 33 for driving the gas sensor 21 is implemented in the hub kernel software 31. It must be noted, though, that driver 33 could also be implemented in the main kernel 30.

A library level 34 sits on top of kernel 30. It comprises a number of libraries, with each library providing functionality that is, at least to a certain degree, typically machine independent (in contrast to the kernel software which is typically adapted to the hardware of the device where it is running). As known to the skilled person, the operating system's runtime is typically implemented in at least one of these libraries.

Each library comprises typically one or more code files comprising code that can be dynamically or statically linked to other libraries or to applications. Typically, libraries are implemented as dynamically linked libraries (DLLs).

One library in library level 34 is the gas sensor control and processing library (GSCP) 35. Its purpose is to control the operation of gas sensor 21 and to process its signals together with and making use of the functions implemented already at the sensor hub level or within the control circuit integrated within the sensor.

On top library level 34 sits the application framework 36, which is typically also implemented as a set of libraries. In contrast to most of the libraries in library level 34, the libraries of the application framework 36 provide a public interface 371 available to the topmost software level, the applications 38. The public user interface 371 is called the Application Programming Interface API and it comprises calling standards (such as header files defining the available functions, classes and methods) as well as binary data (which is part of the libraries in the application framework) that indicates how an application can be dynamically linked to the individual functions and methods within the application framework.

In the present embodiment, part of the application framework is a sensor manager 39, which defines the part of the API that relates to the sensors and which interacts with the sensor-related libraries and drivers in libraries level 34 or in kernel 30.

The applications 38 are typically provided by third parties (i.e. neither by the hardware manufacturer nor by the provider of the operating system). They link against the libraries laid open in the API 371 on order to execute specific tasks.

For example, one such application may be an application that is supposed to detect a certain gas or to analyse the composition of the gases in contact with chemical gas sensor 21. Such an application would use the sensor manager's 39 API in order to interact with chemical gas sensor 21.

A specific interface 372 is provided to allow the GSCP 35 to communicate with a protected part 381 of the file system at the application level. The protected part 381 is accessible from the user level only through a downloader application 382 or the operating system via sensor plugin interface SPI 372.

In another example, the downloading function can be performed by a service of the operating system, residing in the application framework 36, GSCP 35 or kernel 30.

The remote data processing and storage facilities 29 is used in the control scheme of the present example to receive sensor measurement data as measured by the sensor 21. For that purpose the sensor manager can have access to a communication stack of the portable device as indicated by the Network Interfacing Unit NIU 373.

For the purpose of the following description the kernel 30, the libraries 34, and the application framework are denoted as OS to indicate that these parts of the control unit are typically part of an operating system of the portable device. The applications layer 38 is denoted as App level indicating that this layer includes elements such as user installed programs, plugins, setting data, and other personalized data, which can typically be changed without changing the underlying operating system.

Figure 3:
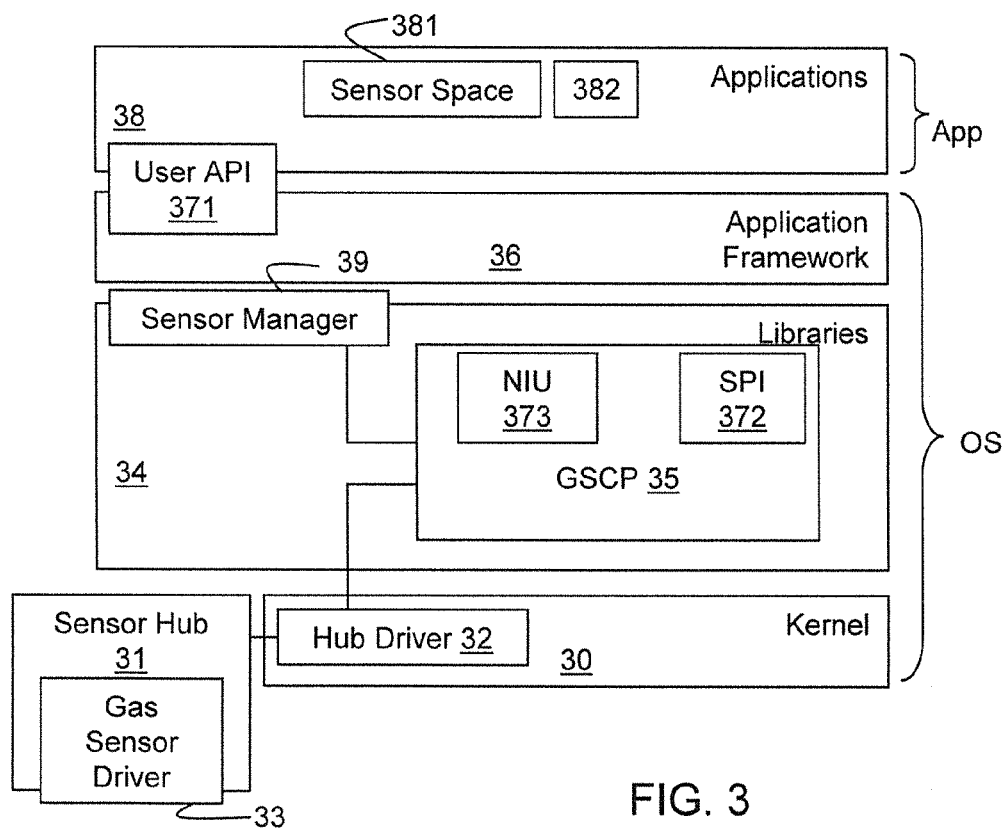
FIG. 3 is a block diagram of a software stack including control elements for a chemical sensor.
Figure 4A:
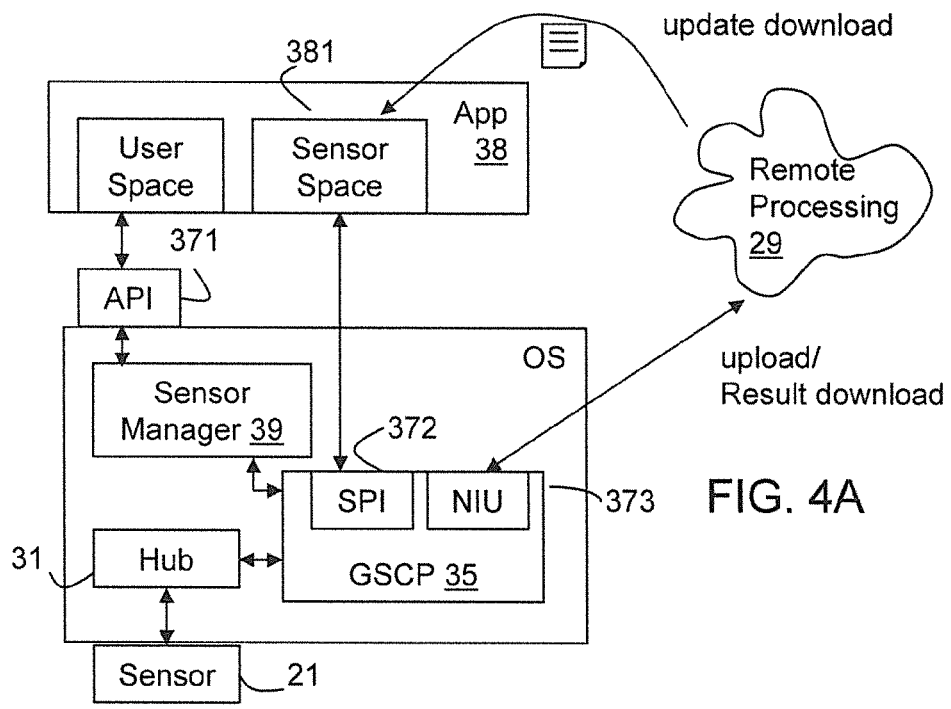
FIGS. 4A-4B illustrate processing steps in accordance with an example of the invention.
Figure 4B:
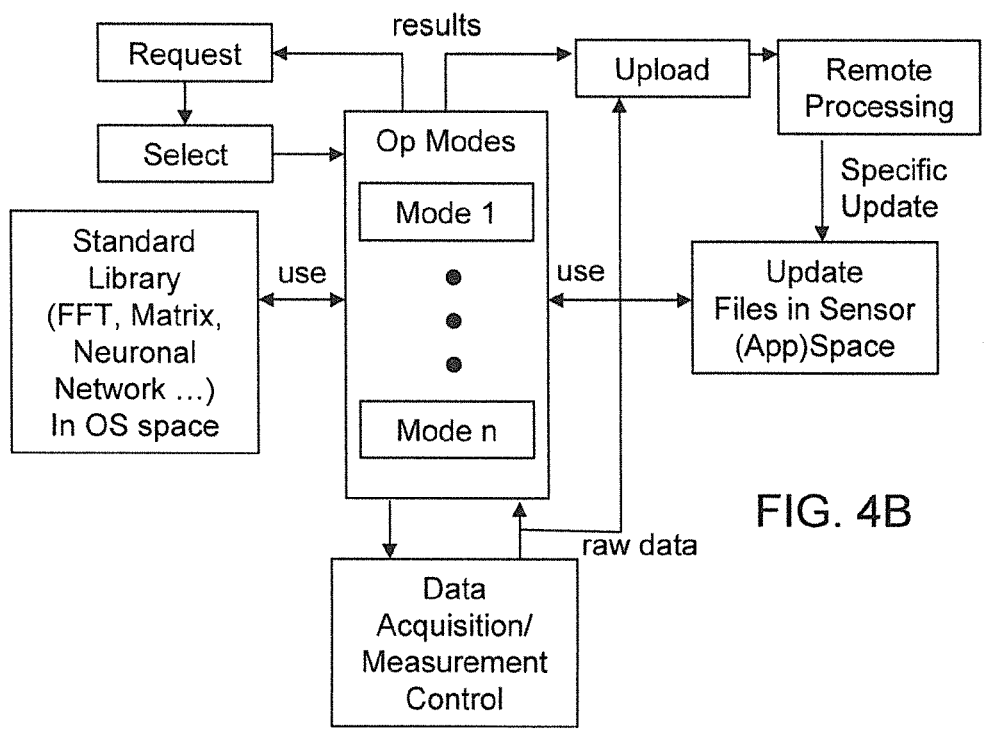

The operation of the above described elements is illustrated in the following referring to the schematic process flow as shown in FIGS. 4A and 4B. The former illustrates the general flow of information between the elements as shown in FIGS. 2 and 3, with the latter providing further details.

A request for a measurement to be performed by the chemical sensor is typically issued by a user application stored in the user space of the App level 38 and transmitted via the User API 371 to the sensor manager 39. The sensor manager 39 dispatches of the request by selecting based on information in the request one or more operation modes 1 . . . n as stored at within the GSCP unit 35. The selected operation mode determines the data acquisition and measurement process, which controls how the chemical sensor 21 is prepared for a measurement, the type of measurement and which signals to return.

As signals acquired in accordance with the selected data acquisition and measurement process are returned as so-called raw data to the GSPC 35 the operation mode selects further data processing steps. The raw data can include for example analogue or digital signals representing resistance values readings from the metal oxide sensor, temperature values, heater current values and the results of parallel sensor measurements such as humidity values. These values can be provided as a single value or a time series of multiple values.

The further processing can include pre-processing steps for the raw data such as applying offset, normalization or scaling, drift or age correction, or linearization. The further processing can include feature extraction steps applied to reduce the raw data into a list or vector of physical properties known to be relevant for the subsequent determination of the result of the measurement.

The result of the measurement is typically a quantification, i.e. a representation of concentration values of one or more gases in the sample, or a qualification or classification indicating the mere presence or absence of one or more gases in the sample, or a combination of both.

To perform the processing steps a number of signal processing routines are stored on the OS level in the portable device, for example as a library. The routines can include basic functions such as baseline corrections, polynomial fits, max-min determination, derivative or integral calculations, spectral analysis such as FFT or DFT, filtering, matrix calculations etc. The routines can further include more complex variants of statistical analysis tools such as Principal Component Analysis, Linear Discriminant Analysis and the like or neural network based tools such as Self-organizing Maps, Back Propagation, pattern recognition routines etc.

As the exact nature of the routines is not seen as a specific aspect of the present example, it suffices to refer to known libraries of such routines as available for example in MATLAB®.

After having performed the processing steps the operation mode typically transfers the result back to the sensor manager 39 to communicate it to the user application via the User API 371, which issued the request for the measurement, for display, storage or further use.

This normal sequence of measurement and processing step as illustrated in the process flow of FIGS. 4A and 4B is accompanied by a transmission step which transfers data to the remote data processing and storage facilities using the NIU 373. The transferred data can include any of raw signals as delivered from the IC of the sensor 21 itself or any pre-processed data fully processed using the GSCP unit 35. The data is transmitted with an identifier of the measuring sensor and/or of the portable device, such that the remote data processing and storage facilities 29 can for example reproduce the processing steps on models representing the specific sensor and/or portable device, in which the sensor is housed. The transferred data can include signals as collected by other sensors of the portable device such as sensors 271, 272, 273. Further signals and data relevant to the chemical measurement can be collected and transferred through other communication links to the remote data processing and storage facilities 29 from sensors and sources exterior to the portable device, for example from other portable devices using the same or similar sensors or any other environmental and location data available.

Given the larger capacity of the facility 29 to perform more complex processing routines and to collect more data a reproduction of a measurement performed locally may result in a different and more accurate analysis. When the remote analysis reveals a systematic error or other ways in which the local processing can be improved, the remote facility can generate an update file or plug-in which modifies the operation of the chemical gas sensor 21.

The content and format of the update file or plugin can vary widely. In general the file includes more than structured and unstructured ASCII text. It typically includes code or instructions for execution either in binary code or in an intermediate language (byte code). By way of example the update file can contain compensation instructions for drift, sensor degradation, recalibration, manufacturing variability compensation. It can also contain parameters altering the standard routines as stored on the OS level, or provide routines replacing those stored with the OS. It can contain instructions altering the sequence of steps and routines used in the signal acquisition, pre-processing and processing as described above.

The update file can be applicable to a group of devices with for example the same type of sensor. But it is seen as a particular advantage of the update file that it can contain information specific to a single portable device and individual sensors within the device. Therefore the update can also include information pertaining specifically to usage of the sensor as per the habits of the owner of the specific portable device.

In order to facilitate such updates, the updates as transmitted from the remote facility 29 is stored in form of or equivalent to an user application on the portable device with the App space 38. Access to the update is provided through the sensor plugin interface SPI 372 such that the GSPC 35 on any equivalent part of the operating system can automatically access data stored as update. The call routines, conditions, settings and flags as well as the correct pointers to the memory location or file containing the updates can be already be predefined and installed with the installation of the OS and/or its sensor specific extensions. The memory location or file can also be protected from other applications by the OS and/or its sensor specific extensions allowing access only from the remote facilities 29 or from a network location acting on behalf of the facilities 29 for the purpose of distributing the updates.

Thus when a personalized update is available, a push notification can be issued by the remote facility and sent to the portable device. Upon acceptance by the user of the device the update is transmitted to the device and stored in accordance with the predefined formats and memory locations. The notification process, the download and storage can be handled by a relatively simple dedicated downloading program 382 stored and run as an application on the portable device. This downloader 382 will have specific authorization to write to the otherwise protected file space. It is also conceivable that the update process is integrated into the operating system 30, 34, 36 similar to the update of applications or calendar information in current operating systems.

With an update file stored and accessible by the GSPC 35 or sensor manager 39, the above process flow is modified in order to take into account the updated routines. Hence, when a user issued request for a chemical measurement is received by the sensor manager 39, the unit are linked via the plugin interface 372 to have access to the update file. Any of the routines used during the signal acquisition, pre-processing and processing are then performed with the update information linked. As a result, the routines are performed in their updated form, if such an update is found.

While there are shown and described presently preferred embodiments of the invention, it is to be understood that the invention is not limited thereto but may be otherwise variously embodied and practised within the scope of the following claims.

The invention claimed is:

1. A method of operating a portable electronic device enclosed in a housing with an integrated chemical sensor linked to a chemical sensor processing unit and being sensitive to the concentration of a component in a sample of air and having an operating system providing instructions for the control of the portable device, wherein the chemical processing unit uses under operating conditions a first set of instructions and a second set of instructions stored within the portable device, wherein the first set of instructions is part of the operating system level of instructions and the second set of instructions is part of a user level of instructions with the second set of instructions being linked to the operating system via an interface and wherein the second set of instructions is communicated to the portable device from a remote computing system based on access to measurements and/or operating conditions of the chemical sensor, wherein storage location used to store the second set of instructions is reserved by the operating system to prevent write access with data not transferred directly or indirectly from the remote system, and wherein the remote system receives sensor measurement data as measured by the chemical sensor;

performs a remote analysis of the sensor measurement data;

generates a personalized update for the chemical sensor based on the received sensor measurement data; and sends the personalized update to the portable electronic device.

2. The method of claim 1, wherein the second set of instructions comprises control or processing routines or parameters for control or processing routines within the first set of instructions as applied to control the operation of the chemical sensor.

3. The method of claim 2, wherein the second set of instructions is applied to select, replace, or alter the performance of the control or processing routines within the first set of instructions.

4. The method of claim 1, wherein the second set of instructions comprises executable code.

5. The method of claim 1, wherein the first set of instructions include an instruction to access the second set of instructions after a measurement of the chemical sensor is initiated at an operating system level.

6. The method of claim 1, wherein modifications or updates of the second set of instructions are independent of and applicable between modifications or updates of the operating system.

7. The method of claim 1, wherein the remote system performs a different, in particular a more accurate, analysis of the received sensor measurement data than the sensor processing unit by performing more complex processing routines and/or by collecting data of other sensors of the portable electronic device and/or by collecting data of sensors and sources exterior to the portable electronic device.

8. The method of claim 1, wherein the personalized update comprises information specific to the portable electronic device and pertaining specifically to usage of the chemical sensor as per the habits of the owner of the portable device.

9. The method of claim 1, wherein the personalized update comprises parameters or instructions altering or replacing the first set of instructions.

10. The method of claim 1, wherein the sensor measurement data is transmitted with an identifier of the chemical sensor and/or of the portable device, such that the remote system can reproduce processing steps on models representing the specific chemical sensor and/or the portable device.

11. A portable electronic device enclosed in a housing with a chemical sensor linked to a chemical sensor processing unit and being sensitive to the concentration of a component in a sample of air and having an operating system providing instructions for the control of the portable device, wherein the chemical processing unit has under operating conditions access to a first set of instructions and a second set of instructions stored within the portable device, wherein the first set of instructions is part of the operating system level of instructions and the second set of instructions being part of a user level of instructions with the second set of instructions being linked to the operating system via an application programming interface, with the device having an assigned memory space for storage of the second set of instructions and a downloader for receiving the second set of instructions from remote computing system based on direct or indirect access to measurements and/or operating conditions of the chemical sensor and for storing the second set of instructions in the assigned memory space, wherein the assigned memory space used to store the second set of instructions is reserved by the operating system to prevent write access with data not transferred directly or indirectly from the remote system, and wherein the remote system receives sensor measurement data as measured by the chemical sensor;

performs a remote analysis of the sensor measurement data;

generates a personalized update for the chemical sensor based on the received sensor measurement data; and sends the personalized update to the portable electronic device.

12. The portable electronic device according to claim 11, wherein the chemical sensor comprises a metal-oxide sensing material.

13. The portable electronic device according to claim 11, wherein the chemical sensor integrated onto a common substrate including CMOS circuitry.

14. The portable electronic device according to claim 11, being selected from a group comprising:
a mobile phone,
a handheld computer,
an electronic reader,
a tablet computer,
a game controller,
a pointing device,
a photo or a video camera,
a digital music player,
an electronic wrist watch,
a headset,
a personal health/fitness tracking device,
and a computer peripheral.

15. The portable electronic device according to claim 11, wherein the remote system performs a different, in particular a more accurate, analysis of the received sensor measurement data than the sensor processing unit by performing more complex processing routines and/or by collecting data of other sensors of the portable electronic device and/or by collecting data of sensors and sources exterior to the portable electronic device.

16. The portable electronic device according to claim 11, wherein the personalized update comprises information specific to the portable electronic device and pertaining specifically to usage of the chemical sensor as per the habits of the owner of the portable device.

17. The portable electronic device according to claim 11, wherein the personalized update comprises parameters or instructions altering or replacing the first set of instructions.

18. The portable electronic device according to claim 11, wherein the sensor measurement data is transmitted with an identifier of the chemical sensor and/or of the portable device, such that the remote system can reproduce processing steps on models representing the specific chemical sensor and/or the portable device.

* * * * *